US008552042B2

(12) United States Patent
Noe et al.

(10) Patent No.: US 8,552,042 B2
(45) Date of Patent: Oct. 8, 2013

(54) USE OF COMBINATION PREPARATIONS COMPRISING ANTIFUNGAL AGENTS

(75) Inventors: Christian Noe, Vienna (AT); Marion Noe, Vienna (AT)

(73) Assignees: Christian Noe, Vienna (AT); Marion Noe-Letschig, Vienna (AT)

( * ) Notice: Subject to any disclaimer, the term of this patent is extended or adjusted under 35 U.S.C. 154(b) by 362 days.

(21) Appl. No.: 12/300,578

(22) PCT Filed: May 10, 2007

(86) PCT No.: PCT/AT2007/000227
§ 371 (c)(1),
(2), (4) Date: Nov. 12, 2008

(87) PCT Pub. No.: WO2007/131253
PCT Pub. Date: Nov. 22, 2007

(65) Prior Publication Data
US 2009/0208558 A1    Aug. 20, 2009

(30) Foreign Application Priority Data

May 12, 2006  (AT) ................................. A 826/2006

(51) Int. Cl.
*A61K 31/35*  (2006.01)
*A61K 31/195*  (2006.01)
*A61F 6/06*  (2006.01)

(52) U.S. Cl.
USPC ........... 514/383; 514/396; 514/459; 514/567; 424/431; 424/432; 424/45

(58) Field of Classification Search
USPC ............ 514/31, 383, 396, 459, 567; 424/431, 424/432, 45
See application file for complete search history.

(56) References Cited

U.S. PATENT DOCUMENTS

| | | | | |
|---|---|---|---|---|
| 5,374,633 A | * | 12/1994 | Parab | 514/171 |
| 2003/0181384 A1 | * | 9/2003 | Podolsky | 514/12 |
| 2004/0142910 A1 | | 7/2004 | Vachon et al. | 514/152 |
| 2005/0014729 A1 | * | 1/2005 | Pulaski | 514/165 |
| 2005/0209266 A1 | * | 9/2005 | Garvey | 514/291 |

FOREIGN PATENT DOCUMENTS

| | | |
|---|---|---|
| EP | 0 592 348 | 4/1994 |
| EP | 1 637 132 | 3/2006 |
| EP | 1 652 535 | 3/2006 |
| JP | 01071823 | * 3/1989 |
| WO | WO 95/017165 | 6/1995 |
| WO | WO 9517165 | * 6/1995 |
| WO | WO 00/028821 | 5/2000 |
| WO | WO 00/48633 | 8/2000 |
| WO | WO 00/56353 | 9/2000 |
| WO | WO 02/03896 | * 1/2002 |
| WO | WO 02/078648 | 10/2002 |
| WO | WO 2005/117831 | 12/2005 |

OTHER PUBLICATIONS

Fichtenbaum et al. (HIV InSite Knowledge Base Chapter (2006) pp. 1-17).*
Faergemann et al. (Clinical Microbiology Reviews, (2002), p. 545-563).*
Scott (Antimicrobial Agents and Chemotherapy, 1995, 2610-2614).*
Arai et al., "Reassessment of the in vitro synergistic effect of fluconazole with the non-steroidal anti-inflammatory agent ibuprofen against Candida albicans," *Mycoses*, 48:38-41, 2005.
Brune et al., "Selektive inhibitoren der zyklooxygenase 2,"*Deutsches Arzteblatt*, 97:A1818-A1825, 2000.
Cannom et al., "Candida albicans stimulate local expression of leukocyte adhesion molecules and cytokines in vivo," *J. of Infectious Diseases*, 186:389-396, 2002.
Filler et al., "Candida albicans stimulates cytokine production and leukocyte adhesion molecule expression by endothelial cells," *Infection and Immunity*, 64:2609-2617, 1996.
Hoffman et al., "Review of the safety and efficacy of voriconazole," *Expert Opinion on Investigational Drugs*, 11:409-429, 2002.
International Preliminary Report on Patentability, issued in Int. App. No. PCT/AT2007/000227, mail date Jan. 22, 2009.
International Search Report, issued in Int. App. No. PCT/AT2007/000227, mail date Oct. 9, 2008.
Klotz, "Adherence of candida albicans to endothelial cells is inhibited by prostaglandin 12," *Infection and Immunity*, 62:1497-1500, 1994.
Kruszewska et al., "Search of antimicrobial activity of selected non-antiobiotic drugs,"*Acta Poloniae Pharmaceutica*, 59:436-439, 2002.
Levy, "Value of benzydamine, the first anti-inflammatory vaginal solution," *Revue Francaise de Gynecologie et D 'Obstretrique*, 84:779-781, 1989.
Scott et al., "Demonstration of synergy with fluconazole and either ibuprofen, sodium salicylate, or propylparaben against candida albicans in vitro," *Antimicrobial Agents and Chemotherapy*, 39:2610-2614, 1995.

(Continued)

*Primary Examiner* — Shirley V Gembeh
(74) *Attorney, Agent, or Firm* — Fulbright & Jaworski LLP

(57) ABSTRACT

The invention relates to the use of an antimycotic agent and an epithelial cell or endothelial cell adhesion inhibitor for producing a combination drug for the topical treatment of *Candida* mycoses selected from vulvovaginal candidiasis, oropharyngeal candidiasis (oral thrush), diaper dermatitis (diaper thrush) and intertriginous (*Candida*) eczema.

8 Claims, No Drawings

(56) References Cited

OTHER PUBLICATIONS

Tariq et al., "Use of decimal assay for additivity to demonstrate synergy in pair combinations of econazole, nikkomycin Z, and ibuprofen against candida albicans in vitro," *Antimicrobial Agents and Chemotherapy, American Society for Microbiology*, 39:2615-2619, 1995.

Yucesoy et al., "In-vitro synergistic effect of fluconazole with nosteroidal anti-inflammatory agents against candida albicans strains," *J. of Chemotherapy*, 12:385-389, 2000.

* cited by examiner

USE OF COMBINATION PREPARATIONS COMPRISING ANTIFUNGAL AGENTS

This application is a national phase application under 35 U.S.C. §371 of International Application No. PCT/AT2007/000227 filed 10 May 2007, which claims priority to Austrian Application No. A 826/2006 filed 12 May 2006. The entire text of each of the above-referenced disclosures is specifically incorporated herein by reference without disclaimer.

The invention relates to the use of combination preparations, comprising antimycotics, for the treatment of *Candida* mycoses. Yeast, primarily *Candida* spp. (*Candida albicans*) usually are opportunistic pathogens which become pathogenic only when the systemic or the local immune defence is impaired (e.g. oral thrush in HIV patients, leukemia patients, under chemotherapy, in babies; intertriginous eczema in Diabetes mellitus). An exception is vulvovaginal *Candida* mycosis of an otherwise healthy woman. However, also with the vaginal candidose there are a number of factors which cause an increase in the virulence of the pathogen, and which, in case of a respective personal disposition, may change from an asymptomatic colonization to a symptomatic disease.

The vulvovaginal mycosis is a very frequent disease which has continuously increased over the last years. According to recent estimates, three out of four women get a vaginal mycosis at least once in their lifetime. In 5% of the cases, the disease takes a chronic-recurrent course which often constitutes a severe subjective impairment for the afflicted patient. Treatment of the vaginal mycosis is particularly difficult during pregnancy, since in this case there exist particularly promoting factors on the side of the patient, while on the other hand the possible therapies are considerably restricted and, thirdly, a therapy is absolutely necessary since otherwise the newborn baby will be infected during birth.

Oro-phyryngeal thrush diseases in turn pose a problem not only in newborns with their immature immune system, but also in patients with an impaired immune defence, such as HIV patients, patients undergoing chemotherapy and patients suffering from malignant hematological tumours. As has been mentioned, it is known that infectious diseases attack debilitated and immunosuppressed humans particularly easily, wherein—as is the case in many diseases caused by *Candida* ssp.—harmless symbionts become pathogens.

Nevertheless, this fact has not been sufficiently mechanistically considered in the therapeutic concept. So far, no drug or combination of pharmaceutical substances in a drug has received a market authorization by means of which the infectiousness of the pathogen on cell level has declaredly been reduced or stopped by influencing physiological reactions of the patient in combination with a direct "attack" on the fungus.

At present, the therapy of cutaneous and mucocutaneous candidiasis is exclusively effected by antimycotics which, depending on the respective dose, have a fungistatical or funcidal effect and, depending on the active substance, are applied systemically or locally.

For the therapy of candida mycoses, such as the thrush of the oral cavity or the vaginal mycosis, a plurality of drugs having an antimicotic effect has been granted market authorization, in most cases for the topical, yet also for the systemic therapy. The mechanism of the pharmacologic activity of nearly all the pharmaceutical substances used is well known. Obviously, most of the known mechanisms are geared to the infective organism (bacterium or fungus) itself. Thus, a number of these pharmaceutical substances interferes in the ergosterole-biosynthesis (isoprene biosynthesis pathway) by inhibition. The pharmaceutical substance attempts to inhibit or kill the fungus via physiological processes that should differ from the human metabolism as far as possible.

In WO 00/56353 A2, peptides derived from alpha-metanocyte-stimulating hormone have been suggested for the treatment of *Candida* vaginitis.

EP 1 637 132 A1 relates to compositions for the treatment of athlete's foot in sportsmen.

EP 0 592 348 A1 discloses compositions for the treatment of ophthalmic diseases.

WO 2005/117831 describes posaconazole-containing preparations for injection for the treatment of mycoses.

According to WO 00/48633 A1, antibodies to hydrophobic proteins have been suggested for combating *Candida* mycoses.

US 2003/181384 A1 relates to administering trefoil peptides for preventing epithelial damage possibly caused by infections. Local anti-inflammatory vaginal rinses containing benzydamine for the mechanical removal of a mass of fungus have been suggested by Levy (Rev. fr. Gynecol. Obstet. 84 (1989), 779-781).

For *Candida* vaginitis, primarily in case of a chronic course thereof, the available spectrum of active agents does not yield any satisfactory option of therapy. This is particularly true if the disease occurs during pregnancy.

The molecular factors underlying the personal disposition are not known in detail, and accordingly, so far there is no drug, or combination of pharmaceutical substances in a drug, with which the infectiousness of the pathogen on cell level is reduced, or stopped, respectively, by a concomitant direct "attack" on the fungus and an influence on the physiological reactions of the patient. Therefore, there is an urgent demand for therapies against *Candida* mycoses which so far cannot be successfully treated by administering conventional antimycotics. In particular, *Candida* mycoses shall be treated which relate to infections of the mucosa, on the one hand, mainly vulvovaginal candidiasis, oropharyngeal candidiasis (oral thrush), and, on the other hand, *Candida* mycosis of previously damaged (macerated) skin, such as diaper dermatitis (diaper thrush), and intertriginous eczema. Such a therapy should also enable treatments of vulvovaginal mycoses in pregnant women which requires a particularly careful use of drugs.

Accordingly, the present invention relates to the use of
an antimycotic agent and
an inhibitor of the adhesion of epithelial cells or endothelial cells, for producing a combination drug for the topical treatment of *Candida* mycoses selected from vulvovaginal candidiasis, oropharyngeal candidiasis (oral thrush), diaper dermatitis (diaper thrush) and intertriginous eczema.

The mycoses to be preferably treated according to the invention have in common that not only the pathogen, but also the afflicted organism (of the patient) contributes considerably to the generation of the disease and to the maintenance of the infection. Apart from the fact that the tendency to contract a disease is basically higher in patients having an impaired immune system, it is the mechanisms of infectiousness which are of particular relevance in this connection. Only in recent years, such concepts have increasingly been investigated in the research regarding anti-infective agents.

The first step determining the infectiousness when a cell is afflicted by a pathogen consists in the pathogen's attachment to the plasma membrane of a cell. In general, a plurality of different systems of adhesion molecules, i.e. cell-cell-interactions, have become known for such an attachment. The general ability of pathogens for adhering to epitheliums and edotheliums also occurs via the interaction with adhesion molecules. For certain pathogens, for certain organs and for certain clinical pictures of diseases, a special set of involved adhesion molecules is to be expected. For infections in general, and mycotic infections in particular, however, adhesion factors which are only partially involved have been published, without, however, having been summarized in a comprehensive concept, or without having been introduced into a therapeutic concept. The present invention is based on the finding that the same adhesion molecules which play a decisive part in the course of the coagulation of blood during the adhesion of the thrombocytes and whose expression is induced by derivatives of the arachidonic acid metabolism (inter alia von Willebrand-factor, vitronectin, fibronectin, integrins), are induced during the transformation to pathogenicity by accompanying factors or the pathogen itself and, subsequently, are utilized for the adhesion by the primarily opportunistic pathogens.

It has been known for quite some time that under the influence of prostaglandins, *Candida* fungi undergo a transformation of their shape from budding shape to hyphae shape which is accompanied by an increased growth. Prostaglandins are derivatives of arachidonic acid. The active principle of the class of pharmaceutical substances of the NSAIDs, which are mainly used for the treatment of inflammatory and rheumatic diseases, primarily consists in the inhibition of the prostaglandin biosynthesis. The influence of NSAIDs on the growth of fungi has been demonstrated in in vitro experiments (Scott et al., Antimicrob. Ag. Chemother. 39 (12) (1995), 2610-2614; Tariq et al., Antimicrob. Ag. Chemother. 39 (12) (1995), 2615-2619; Yucesoy et al., J. Chemother. 12 (2000), 385-389). In this combination with anti-mycotic agents, an increase in the anti-mycotic effect has occasionally been observed, yet the term "paradox effect" has been explicitly established for this, since, in vitro, at some concentrations and in some combinations, instead of an inhibition there results an increased growth (Arai et al., Mycoses 48 (2005), 38-41). Thus, the effects of Ibuprofen in combination with various antimycotics have been very varied (Tariq et al., 1995). Fluconazole-sensitive strains of *C. albicans* have not shown an improved response to a combination of Ibuprofen with Fluconazole in the in vitro-system (Arai et al., 2005). In summary, the results of the in-vitro tests have shown that, based on the growth of the fungus, the effects depend on the respective fungus strain used, yet that from these no conclusions can be drawn on the medical efficacy at the site of the mycotic infection, neither in the one (positive) nor in the other (negative) direction.

Since usual in-vitro experiments regarding an anti-mycotic activity of certain substances or substance combinations do not take the physiological response of the host into consideration, in none of these in-vitro projects, the part which the cell-cell adhesion plays in the infection in general, or changes occurring in the host's epithelium or endothelium, respectively, can have been addressed in the least.

Moreover, in the relevant literature, the therapy resistance occurring in the treatment of chronic-recurrent *Candida* vulvovaginitis i.a. has been attributed to the increased occurrence of certain *Candida* subspecies (without, however, offering a conclusive total concept). Yet, especially for these subspecies, no in vitro-results whatsoever are available.

In case of *Candida*, in fact the transformation of the growth habit from the budding form to the hyphae form is a prerequisite for the layer-type overgrowth. This clearly intensifies the pathogenicity of the pathogen. The formation of the hyphae in turn is promoted by prostaglandin E2 which is also formed by the patient's endothelial cell/epithelial cell during the inflammatory process. Also the increased mucus formation of mucous membranes occurring during the inflammatory process plays a part in this pathological process.

Under certain promotive conditions in the microenvironment, such as, e.g., an impaired immune situation, yet also in case of suitable hormonal conditions or a patient's genetic disposition or, on the other hand, due to quorum sensing, some pathogens, such as, in particular also *Candida* species, are capable of overgrowing the affected sector of the skin, mucosa or endothelium by forming a closed layer. This not only aggravates the pathological process; due to the transformation of the growth habit, also the pathogen's vulnerability by local treatment methods changes. In this growth habit, the pathogens practically can no longer be attacked by the usual locally applied anti-mycotic agents. Chronification occurs, and it becomes necessary to change from a local therapy to a systemtic therapy. A systemic antimycotic therapy, however, often constitutes a great strain due to the spectrum of side effects of many antimycotic agents and, in case of pregnant women, it is completely impossible because of teratogenic effects. Yet, even under systemic therapy, the chronic-recurrent vulvovaginitis and colpitis caused by *Candida* spp. (with *Candida albicans* and *Candida glabrata* being the most frequent pathogens) often are not cured, and many female patients suffer from several recurrences each year.

The present invention is based on the so far unknown finding which, however, is central with regard to infectiousness that, when attaching to epithelial cells (or to endothelial cells, respectively), yeast fungi use arachidonic-acid-based mechanisms of the body itself, by which the organism usually reacts to cell-damaging noxae.

Arachodonic acid is known to be converted on the cyclooxygenase pathway not only to prostaglandins, but also to thromboxane and prostacycline. Under the influence of thromboxane, the thrombocytes aggregate and adhere to the damaged membrane so as to seal the latter. In order to enable an adhesion, different adhesion molecules are not only presented by the thrombocyte; also the endothelium specifically prepares itself for the adhesion. On molecular level, these effects are primarily mediated via adhesion molecules, such as, e.g., von Willebrand factor. The processes taking place during the adhesion occur temporally adjusted in the thrombocyte and in the vessel endothelium. It is mainly two derivatives of the arachidonic acid cascade which play a decisive role as adversaries in the process of blood coaguation: besides thromboxane which causes the aggregation of thrombocytes, it is the "adversary" prostacyclin which prevents the reactive process from spreading excessively. The biosynthesis of thromboxane and prostacyclin is mediated by different enzymes.

Thromboxane is synthesized via cyclooxygenase-1 (COX1), prostacyclin via cyclooxygenase-2 (COX2).

An essential element of the mycotic infection consists in that the fungus/host interaction comprises a series of mechanistic analogies to the thrombocyte/endothelium interaction. Primarily, this means that inflammatory processes occur in the host cells either before or simultaneously with the mycotic infection, i.e. the transformation of apathogenic, or possibly pathogenic, respectively, to pathogenic causative agent (e.g. Filler et al., Inf. Immun. 64 (1996), 2609-2617; Cannom et al., J. Inf. Dis. 186 (2002), 389-396), which are controlled via the arachidonic acid cascade, or that the adhesion of the fungus is rendered possible at all by previous inflammatory processes in the host cell. On the part of the fungus, adhesion of the fungi to the host cells occurs via the hyphae, on the part of the host cell, it is substantially effected via an arachidonic-aciddependent mechanism, utilizing the adhesion molecules expressed under these conditions at the host cell, such as, e.g., von Willebrand factor, vitronectin, fibronectin or various integrins.

Providing an epithelial cell or endothelial cell adhesion inhibitor in the combination preparation according to the present invention is, therefore, an essential element for the anti-mycotic agent to become effective at all in the infected area of the *Candida* mycoses to be treated according to the invention. The nature of the epithelial cell or endothelial cell adhesion inhibitor as such is not critical, the selection is generally dictated by galenic aspects for (promoting an) optimal activity of the antimycotic agent. Therefore, antimycotic agent and epithelial cell or endothelial cell adhesion inhibitor are optimized in the combination preparation also on the basis of their physico-chemical properties. This adhesion inhibitor according to the invention exerts an influence on the arachidonic acid metabolism so that the inventive combination is capable of synergistically acting on the mycotic infection at the site of infection and by utilizing the patient's endogenous arachidonic acid mechanisms.

Preferably, therefore, the epithelial cell or endothelial cell adhesion inhibitor is selected from
- a non-steroidal antiphlogistic agent (NSAID) with a sufficient COX1 inhibition which, on the one hand, results from the intrinsic activity and, on the other hand, from the extent of the selectivity of the inhibition of COX1 relative to COX2 under therapeutic conditions. This means that all the substances which exhibit a more selective COX2 inhibition than, e.g., Meloxicam or Diclofenac, are not suitable as defined by the invention (such as, of course, also all the substances which do not exhibit any activity or effects on the arachidonic acid metabolism). The selection in terms of number is effected, e.g., by stating the COX1/COX2 ratio of the IC50 values, yet this will differ with the method used. Suitable compounds may, e.g., be defined in terms of numbers in accordance with the data supplied by K. Brune et al. (Deutsches Ärzteblatt 97, (26) 2000, A-1818/B-1538/C-1434) by a COX1/COX2 ratio (IC50) of ≤20,
- prostacyclin or a prostacyclin analogue, preferably Ilaprost or Cicaprost; or
- inhibitors of the expression of epithelial- and endothelial adhesion molecules, preferably Ticlopidin or Clopidogrel.

These three categories constitute the main inhibitors of epithelial cell or endothelial cell adhesion. For all the three groups, substances at present already have a market authorization or are in an advanced-stage clinical study.

Therefore, in the combination preparation according to the invention drugs are preferably contained which inhibit the thrombocyte aggregation, such as mainly NSAID with COX1-inhibition, or medicaments which prevent the expression or the function of adhesion molecules in the endothelium connected with this process, which exacerbate or prevent the adhesion of pathogens to the endothelium or epithelium, respectively in an analogous manner. This is not only effected via the suppression of the expression of suitable adhesion molecules, but mainly also by triggering/increasing the shedding of these surface molecules. In the same way, prostacyclin itself and prostacyclinderivatives are capable of reducing or stopping the adhesion. The inventive use of such compounds in combination with an anti-mycotic agent thus both prevents the infection, and also prevents the "boosting" of the infection triggered by inflammatory processes occurring in the course of the infection. The finding that such a complex process as the adhesion of a fungus to the endothelium of the host can be influenced by active substances of a well-known class has not been known so far and forms the basis of the combination preparations according to the invention by which the surprising clinical results according to the present invention could be achieved, in particular in case of the preferred *Candida* mycoses described which so far could not be treated or could be treated only with difficulty.

The inventive combinations of pharmaceutical substances are intended for topical application (at mucosae or also on highly inflamed skin areas, such as in case of diaper thrush, and intertriginous eczema) for treating mycoses (vulvovaginitis oropharyngeal candidiasis (oral thrush), diaper dermatitis intertrignious eczema) and, as mentioned before, consist of an anti-mycotic agent and an adhesion inhibitor of epithelial cells or endothelial cells, which inhibitor exacerbates, or prevents, respectively, the adhesion of the pathogen to the epithelial and/or endothelial cells and the formation of a layer-shaped colonization of the affected epithelial or endothelial sector, by suppressing the above-described mechanisms.

As has been mentioned above, it is particularly preferred to use an NSAID compound. Yet, not all the NSAIDs are suitable compounds in the combination preparation according to the present invention, since NSAIDs, depending on their profiles (COX1-inhibitor or COX2-inhibitor), generally have a promoting (COX2) or inhibiting effect (COX1) on an adhesion. For this reason, the treatment of dermatologic diseases with a combination that contains a selective COX2-inhibitor (such as, e.g., disclosed in US 2005/0014729 A) is wrong with regard to the therapeutic aim of the present invention, i.e. causing the reduction of the adhesion in the patient's endothelium or epithelium. Highly selective COX2 inhibitors or anti-inflammatory agents without an activity on the arachidonic acid mechanism (such as, e.g., benzydamine (Riboldi et al., Br. J. Pharmacol. 140 (2003), 377-383)) are no relevant compounds as defined by the present invention.

The selectivity of the NSAID is, e.g., expressed by the ratio of the IC 50 (microM) COX1/COX2, yet the values will generally depend on the pharmacological test systems used and will differ greatly, and therefore, according to the invention, the values are determined in terms of numbers according to the data given by K. Brune et al. (Deutsches Ärzteblatt 97, (26) 2000, A-1818/B-1538/C-1434).

What is essential for the therapeutic effectiveness is a sufficient COX1-inhibition (absolute value of the IC 50) at the respective administered therapeutic dose. Most of the NSAIDs are mixed COX1/COX2-inhibitors. As long as there exists a COX1 inhibition, the COX2-inhibition is very welcome (because of the suppression of pain). Therefore, NSAIDs without or with only a slight preference of the COX2 are substances to be used according to the invention. Not suitable are, however—as mentioned before—(highly) selective COX2-inhibitors which do not have a COX1 effect or have only an insufficient COX1 effect under therapeutical conditions (dosages). On the contrary, the selective COX2 inhibitors may even negatively affect the clinical picture and, therefore, are to be avoided within the scope of the therapy according to the invention. Therefore, according to the invention NSAIDs which have a value of >20 for the COX1/COX2-ratio (based on the above-cited literature) are to be excluded (for highly-selective COX2-inhibitors with a market authorization, values of more than 100 result, e.g. Celecoxib, Rofecoxib, Valdecoxib, Etoricoxib).

Accordingly, the NSAID in the combination preparation according to the present invention preferably is selected from Diclofenac, Fenclofenac, Alclofenac, Lonazolac, Clidanac, Oxipinac, Clopinac, Tolmetin, Indomethacin, mefenamic acid, flufenamic acid, meclofenamic acid, tolfenamic acid, niflumic acid, Floctafenin, bucloxic acid, Ibuprofen, Dextroprofen, Prapoprofen, Miroprofen, Fenoprofen, Fluprofen, Flurbiprofen, Ketoprofen, Alminoprofen, Tioxaprofen, tiaprofenic acid, Isoxepac, Nimesulid, Meloxicam, Tenoxicam, Lornoxicam, Piroxicam, Droxicam, Sudoxicam, Naproxen, Bufexamac, Etofenamate, Felbinac, Nabumeton, Ketorolac, Etodolac, Oxaprocin, salicylic acid, acetylsalicylic acid, Flufenisal, Diflunisal, Benorylat, Fentiazac, Azapropazon, Phenylbutazone, Kebuzon, pharmaceutically active salts or esters of these substances or mixtures of these substances, in particular Diclofenac, Nimesulid, Fenclofenac, Alclofenac, Lonazolac, Tolmetin, Indometacin, mefenamic acid, flufenamic acid, meclofenamic acid, Floctafenin, Ibuprofen, Flurbiprofen, Ketoprofen, Alminoprofen, Meloxicam, Tenoxicam, Lornoxicam, Naproxen, Etofenamate, Felbinac, Nabumeton, Ketorolac or Etodolac.

The particular significance of the combination according to the invention of an antimycotic agent and an adhesion inhibitor of epithelial or endothelial cells will directly depend on the extent of the effect of the second component which primarily contributes to the therapeutic effect by an adhesion-suppressing effect on the patient's endothelium and/or epithelium. Therefore, it is of particular importance to consider that the term "skin diseases" covers a broad range of skin tissues of completely different structures: from an adult's nail to a baby's mucosa. What is common to all the diseases which have been mentioned as preferred indications for the combination preparation according to the present invention (vulvovaginal candidiasis, oropharyngeal candidiasis (oral thrush), diaper dermatitis (diaper thrush) and intertriginous eczema) is that it is the surface of the afflicted tissue sectors which, due to the expression of corresponding adhesion molecules, enables an adhesion of the fungal colonies. The combination preparation according to the invention serves for the therapy of mycoses, preferably for the therapy of *Candida* mycoses which, typically, occur on the aforementioned skin types, i.e. mucosae of the genitourinary tract and the oropharyngeal region as well as on previously damaged (macerated, injured, inflammatorily changed) outer skin.

Accordingly, it is not a subject matter of the present invention to carry out a therapy of dermatophyte diseases (EP-1 390 031-B1) with the combination preparation described, which diseases often colonize the keratic layers of the epidermis, since there the contribution to the therapeutic success which is provided by preventing the adhesion of the fungus to the host's epithelium is markedly lower and, therefore, the inventive effect will not occur. This also holds, e.g., for the treatment of mycoses of the nails (WO 2000/028821 A1), since here, too, the use of the inventive combination preparation is not purposeful since, here, too, the surprising synergism of the two components in the inventive preparation will not occur (to the inventive extent), in particular because in this instance the state of the epithelium is of minor importance compared to the particularities of the therapy of these diseases, in particular the poor "accessability" of the therapeutic agent.

For the topical therapy according to the invention with the described combination drug on mucosae or previously damaged outer skin, respectively, according to the invention not only significantly lower concentrations of the active substance will basically suffice as compared to diseases of the normal or more keratinized outer skin and its adnexa, also a significant improvement of the subjective and objective disease symptoms will occur within a substantially shorter time (from minutes to a few hours vs. from days to weeks when applying the treatment methods common at present). Thus, the particularly low dosage of the adhesion-inhibiting active substance is a substantial advantage with the present invention. This rapid start of the effectiveness is solely caused by the procedures on the skin or mucosal surface that has been changed due to inflammation and, therefore, can be forecast or determined in principle neither by in vitro-tests nor by examinations on the non-inflamed outer skin. Since the greatly enhanced effect is caused solely based on mechanisms occurring on the exposed surface of the respectively afflicted organ (expression and rejection of the adhesion sites), particularly also this effect cannot be determined by in-vitro experiments, and, in fact, it has been shown that in-vitro experiments, depending on the fungus strain used, the dosage and the combinations of pharmaceutical substances used, have yielded the most contradictory results. In this context, it is also notable that the combination of Fluconazol with Ibuprofen in Fluconazol-sensitive strains has not shown any synergistic effect in the in-vitro experiment (Arai et al., 2005). The effect obtainable with the combination preparation of the invention therefore also cannot be derived in this way (via in-vitro experiments). Also in case of a systemic administration of the inventive combination preparation, in particular of the epithelial cell or endothelial cell adhesion inhibitor (i.e., e.g., the NSAID chosen according to the invention), for pharmacokinetic reasons a respective effect is not to be expected even at a common dosage, and much less so at the low dosages which are made possible with the present invention.

The required low dose is also due to the fact that the epithelial cell or endothelial cell adhesion inhibitor exerts its effect both on the fungus and on the epithelium of the patient.

Thus, also a treatment of breastfeeding babies and of pregnant women is possible.

Thus, the effect of the inventive combination of pharmaceutical substances is based on
1. suppressing pathogen growth,
2. suppressing adhesion of the pathogen on the host cell,
3. suppressing the acute inflammation and pain symptoms by inhibiting the prostaglandin synthesis on the part of the afflicted organism,
4. preventing the generation of the promotive factors in the local environment, i.e. the adhesion to the host cell upon transformation of the pathogen and, thus, preventing an aggravation of the clinical picture, and
5. interrupting the pathogenetic mechanism in case an aggravation/chronification has occurred,
wherein 2.-5. are mediated by the epithelial cell or endothelial cell adhesion inhibitor (which interferes in the arachidonic acid cascade) and 1. is mediated according to the mechanism of activity of the antimycotic agent used.

This allows for a therapy concept which is completely new as compared to the prior art, which—apart from the effectiveness which by itself already is surprising in (chronic-recurrent) vulvovaginal candidiasis, oropharyngeal candidiasis (oral thrush), diaper dermatitis (diaper thrush) and intertriginous eczema—is, moreover, characterized by the following advantages and effects compared to the prior art:
1. possibility of a local therapy,
2. in case of chronification, marked reduction of the tendency to recurrence,
3. highly accelerated onset of effect,
4. significantly reduced dosage of the antimycotic agent, and
5. immediate pain relief.

Ad 1. In case of promotive factors, in particular also for an aggravation/chronification, e.g. an immunosuppression, hormonal and genetic factors, according to the present invention the pathogenetic mechanism on which the disease disposition is based is inhibited. The disease can be controlled, and cured, respectively, without a systemic therapy. Avoiding the changeover to a systemic therapy (which often is effected by using pharmaceutical substances that are a greater strain) is important both in case of an existing pregnancy and in patients suffering from HIV, leukaemia or under chemotherapy and markedly reduces the strain on the patient, according to both subjective (compliance) and objective criteria (strain on the metabolism). The chronic-recurrent vulvovaginitis in pregnancy can hardly be controlled by means of the conventional therapy regimen, since the systemic application of the orally applicable antimycotic agents (Fluconazol) is absolutely counter-indicated in pregnancy.

Ad 2. Also in case of a chronic-recurrent course of the disease (in particular in case of vulvovaginitis due to *Candida* infections), the underlying pathogenic mechanism is interrupted, and a topical therapy is rendered possible instead of the long-lasting systemic therapy.

Ad 3. Compared to the hitherto usual therapy, the onset of the effect is greatly accelerated, i.e. it occurs within minutes (vulvovaginitis) to hours (diaper thrush) as compared to days to weeks (or not at all) in conventional therapy.

Basically, the difference resides mainly in the duration of treatment, the therapy regimen proper will, however, first of all depend on the half-life of the pharmaceutical substances used. The difference may, e.g., be elucidated by way of the chronic-recurrent vulvovaginitis:

Use According to the Invention:
Initial therapy: 3-5× daily local application of the drug combination as an ointment, or by means of another locally applicable drug formulation for three to five days;
in case of recurrent affliction: 2-3× daily local application for one day is sufficient (the recurrence-free intervals will always become longer with continued application).

In contrast, the present therapy regimen (source: Leitlinien der deutschen Gesellschaft für Gynäkologie und Geburtshilfe):
Initial Therapy:
Fluconazol 150 mg orally, 1 or 2×/week for 4-6 weeks, subsequently
Fluconazol 150 mg orally, 1×/2 weeks for 2-3 months, subsequently
Fluconazol 150 mg orally, 1×/4 weeks for 4-6 months.
After discontinuation, about 50% of the cases become recurrent, as before the therapy.

Ad 4: Due to the potentiating effect, the total dose of the antimycotic can be markedly reduced, in case of the uncomplicated vulvovaginal mycosis, one can assume a by at least 50% reduced total dose due to the reduced treatment period, in the oropharyngeal mycosis, the reduction may be up to 66%.

Ad 5: With the often very painful acute clinical pictures, by the simultaneous topical application of NSAID with the antimycotic agent, an immediate pain relief and detumescence with missing to minimal total strain on the organism is achieved with the NSAID (non-steroidal antiphlogistic agents) which, systemically applied, are not free from side effects. As has been mentioned, the treatment according to the invention is based on the finding that the expression of certain adhesion molecules at the tissue surface of the diseased organism or organ, respectively, constitutes a basic prerequisite for the colonization by yeasts. The combination of conventional antimycotic agents with epithelial cell or endothelial cell adhesion inhibitors therefore directly interferes in the pathogenetic process. As has been mentioned, epithelial cell or endothelial cell adhesion inhibitors are substances which exacerbate or prevent, respectively, the adhesion of the pathogens to epithelial and/or endothelial cells and the formation of a layer-shaped colonization of the afflicted epithelial or endothelial sector. From the nature of the responsible adhesion molecules it results that their expression is prevented by active substances which interfere in the prostaglandin metabolism in a certain way. From the inventive combined application of antimycotically effective substances and epithelial cell or endothelial cell adhesion inhibitors, there results a potentiation of the therapeutic effect. The duration of treatment is greatly shortened, and a local treatment becomes possible also in those cases in which so far exclusively a systemic therapy had chances of success. Moreover, this type of a combination of pharmaceutical substances also is effective in cases which are completely therapy-resistant to drugs available at present.

Therefore, the subject matter of the invention is the use of the inventive combinations of pharmaceutical substances for the topical application on mucosae and on greatly inflamed and/or macerated skin areas for the treatment of mycoses, preferably those caused by *Candida* spp. (vulvovaginitis, oropharyngeal candidiasis (oral thrush), diaper dermatitis (diaper thrush), intertriginous eczema).

Application of the inventive combination preparation is exclusively local (ointments, vaginal tablet, vaginal suppositories etc.) to skin and mucosae. The dosage of the antimycotic agent (preferably Clotrimazol) is effected at the concentration hitherto common, yet the daily total dose can be halved, and the total treatment time is markedly reduced (from 7 to 2-3 days). The epithelial cell or endothelial cell adhesion inhibitor is administered at $1/5$ to $1/100$ of the daily maximum dose as an admixture to the ointment/vaginal tablet etc.

During the topical therapy with an inventive combination of pharmaceutical substances, as mentioned above, the total amounts of active substance that are substantially lower than those hitherto used in the antimycotic monotherapy suffice, and also the NSAID component is used at a significantly lower concentration than in all other indications for which so far drugs of such substances have been used. Thus, also a treatment of breastfeeding babies and pregnant women is possible.

Within a substantially shorter period of time (from minutes to a few hours, as compared to from days to weeks when using the treatment methods common at present), a significant improvement of the subjective and objective disease symptoms will occur. This rapid onset of the effect is solely caused by the processes at the surface of the mucosa and goes back to the effect of arachidonic acid derivatives triggered at the afflicted organ surfaces and, therefore, can neither be detected in in-vitro tests nor by examinations carried out on the normal outer skin.

The nature of the antimycotic active substance to be employed in the present combination preparation in principle is not critical, as a rule, always an optimized combination pair will be used, wherein the optimization primarily is based on the antimycotic spectrum of the antimycotic agent, on the galenics and on the physoco-chemical interactions of the anti-mycotic agent with the epithelial cell or endothelial cell adhesion inhibitor.

Preferred are, of course, those antimycotic agents which already have a market authorization.

Therefore, the antimycotic agent in the combination preparation according to the invention preferably is an azole or a conazole, preferably Clotrimazole, Bifonazole, Croconazole, Miconazole, Econazole, Isoconazole, Itraconazole, Fenticonazole, Tioconazole, Sertaconazole, Sulconazole, Omoconazole, Oxiconazole, Fluconazole, Voriconazole or Ketokonazole, in particular Clotrimazole and Miconazole, a squalene epoxidase inhibitor, preferably Naftifin or Terbinafin, or an antibiotic, preferably Nystatin, Amphotericin B, Capsofungin or Natamycin, or Tolciclate, Tolnaftate, Ciclopirox, Haloprogin, Butenafine, Flucytosine.

Preferably, the combination drug according to the present invention is prepared as ointment, cream, lotion, gel, tincture, solution, vaginal suppository, vaginal, buccal or sublingual tablet, syrup, suspension, powder, spray or aerosol.

According to a preferred embodiment of the present invention, the combination drug may be provided on an inert carrier, in particular on a vaginal ring, a diaphragm or a tampon.

The invention will be described in more detail by way of the following examples without, however, being restricted thereto.

Examinations and Results on Humans—Case Studies

So far, the therapy concept according to the invention has been examined on voluntary subjects within the frame of the doctors' freedom of prescription. Before the combination therapy, all the patients had received an unsuccessful antimycotic monotherapy.

In the following, 6 examples will be described:
vulvovaginitis: 3 cases
diaper thrush: 2 cases
oral thrush: 1 case The treatment was by topical administration of suitable pharmaceutical substance combinations on the skin, or on the mucosae of the genitourinary tract and of the oropharynx, respectively.

The following combinations were used:
Vulvovaginitis:
 Case 1:
 A female 41-year old patient suffering from chronic-recurrent *Candida* vulvovaginitis for years (>10 recurrences/year), otherwise healthy, pregnant, prior treatment (before the pregnancy) both topical (Clotrimazole, Nystatin) and systemically (Fluconazole, several times, also long-term therapy and therapy of the partner). Massive deterioration with complete therapy resistance to local treatment with Clotrimazole during pregnancy, extreme subjective complaints for weeks.
 Gyn. findings: vulva severely reddened, clearly swollen, bloody excoriations. Mucosa of the vagina and portio reddened. Massive vaginal discharge, smear findings: PAP 2., microbial. swab, native finding: abundant leukocytes, fungus hyphae detectable in large masses, RG 3.
 Therapy with an ointment combination of Clotrimazole/Diclofenac-Na
 Single dose: 5 mg of Diclofenac-Na/20 mg of Clotrimazole
 Dosage regimen: initially (3 days) 3×/day ointment strips of 2.5 cm locally applied in vulva and vagina, subsequently once per day, for 4 days.
 The applied dose (total dose) of Diclofenac-Na is approximately 1/30 of the maximum daily dose at systemic application. The Clotrimazole dose is one half of the usual daily dose.
 Findings after one week of therapy (three days after termination of therapy):
 Patient subjectively free from complaints, (since beginning of therapy). Gyn. findings: vulva: results negative; mucosae of vagina and portio: results negative. Low-grade vaginal discharge. Microbiol. swab, native findings: no fungus hyphae detectable, isolated spores. Normal vaginal flora (lactobacilli), RG 1.
 Follow-up: 6 months
Over the next three months, approximately 2 recurrencies/month, one-day treatment as above in each case resulted in immediate freedom from complaints.
Following months: complete freedom from complaints, no new recurrences.

Case 2:
 43-year old female patient, suffering from chronic-recurrent *Candida* vulvovaginitis for years (>10 recurrences/year), otherwise healthy, prior treatment both topical (Clotrimazole, Miconazole) and systemically (Fluconazole, several times, also long-term therapy and therapy of the partner). Acute exacerbation, low-grade improvement under therapy with Clotrimazole (8 days), partly extreme subjective complaints for 2 weeks.
 Gyn. findings: vulva severely reddened, clearly swollen. Mucosa of the vaginal and portio reddened. Massive vaginal discharge.
 Initial therapy: Clotrimazole/Diclofenac (25/25 mg) supp. for 2 days, subsequently
 Clotrimazole/Diclofenac as ointment as described in Case 1, for 3 days.
 Findings after 1 week: patient subjectively free from complaints (since $2^{nd}$ day after beginning of therapy). Gyn. findings: vulva results negative; mucosae of vagina and portio: results negative. Low-grade vaginal discharge.
 Case 3:
 42-year old female patient, suffering from chronic-recurrent *Candida* vulvovaginitis for years (>10 recurrences/year), otherwise healthy, prior treatment both topical (Clotrimazole, Nystatin) and systemical (Fluconazole, several times, also long-term therapy and therapy of the partner). Acute exacerbation, during this recurrence no pre-treatment, moderate subjective complaints for 2 days.
 Gyn. findings: vulva reddened, swollen. Mucosa of the vaginal and portio reddened. Increased vaginal discharge.
 Therapy: Clotrimazole/Diclofenac as ointment as described under Case 1 on the first day 5×/day, from the $2^{nd}$ day onward 3×/day for a total of three days.
 Findings after 1 week: Patient subjectively free from complaints (since 18 hours after the beginning of therapy). Gyn. findings: vulva results negative; mucosae of vagina and portio: results negative. Low-grade vaginal discharge.
 Case 4:
 Diaper Thrush:
 Female breastfeeding baby, 12 months old, therapy-resistant eczema for more than 5 weeks at the labia majora (pretreatment by paediatrician and dermatologists with: zinc-oxide containing baby cream, Nystatin-containing cream, antibiotic (antibacterial) cream and powder, Clotrimazol-containing cream, corticosteroids. Under these therapies, continuous deterioration of the clinical picture.
 Insp.: Pronounced reddening and swelling of the labia majora and perianally.
 Therapy with an ointment combination of Clotrimazole/Diclofenac-Na
 Single dose: ointment strips of approximately 5 cm in the evening (corresponding to approximately 10 mg of Diclofenac-Na/40 mg Clotrimazole), complete healing over night. Subsequently, intestinal sanitation with Nystatin, oral suspension.
 Follow-up (6 months): no further complaints
 Case 5:
 Diaper Thrush:
 Female breastfeeding baby, 2 months old, repeated diaper thrush (red papules).
 Insp: Small papules on the skin of the labia majora and in the perianal region.
 Therapies tested: during various episodes, comparison of Clotrimazole cream with and without the addition of Diclofenac-Na.
 Monotherapy: Clotrimazole cream (Canesten), single dose: approximately 25 mg of Clotrimazole Combination: Clotrimazole/Diclofenac-Na, single dose: approximately 5 mg of Diclofenac-Na/20 mg of Clotrimazole.
In both cases, local application, dosage: 4-5×/day.
Result:
Monotherapy: duration of treatment until complete disappearance of the lesions: 3 days.
Combination therapy: duration of treatment until complete disappearance of lesions: 24 hours.
  Case 6:
  Oral Thrush:
  Female breastfeeding baby, 2 months old, repeated oral thrush (white lesions).
Insp.: typical white furs on the inner side of the upper and lower lips, diameter 4-5 mm.
  Therapies tested: during various episodes comparison of Miconazole gel with and without the addition of Mefenamic acid.
Monotherapy: Miconazole (Daktarin gel), single dose 30 mg
Combination: Miconazole/mefenamic acid (gel).
In both cases local application, dosage: 2-3×/day
Single dose: approximately 25 mg of mefenamic acid/30 mg of Miconazole
  Result:
Monotherapy: duration of treatment until complete disappearance of the lesions: 5 days
Combination therapy: after 12 hours, significant reduction of the lesions, duration of treatment until complete disappearance of the lesions: 24 hours.
  Summary of the Results of the Single Case Studies:
  Vulvovaginitis: The cases described were particularly severe cases of chronic-recurrent *Candida vaginitis*. Under monotherapy with Clotrimazole, the course of curing was highly retarded in the second case (8 days of intensive therapy, then improvement, but no freedom from complaints), in the first and third cases no improvement could be achieved by conventional local therapy with Clotrimazole. By using the pharmaceutical substance combinations, an immediate marked improvement of the subjective and objective symptoms occurred, and already on the second day of treatment, in all the cases the complaints completely disappeared.
  Diaper thrush: Under Clotrimazole monotherapy, marked deterioration of the clinical picture in the first case, healing after three days in the second (mild) case. Complete healing after the use of the pharmaceutical substance combination within 12 and 24 hours, respectively.
  Oral thrush: healing with Miconazole monotherapy after 4-5 days (criterion of diagnosis: no plaques visible any longer in the oral cavity). During a second episode, treatment with the pharmaceutical substance combination, no plaques visible any longer after two hours.
  These results show that in case of *Candida* mycoses which are particularly difficult to treat, the combination preparation of the invention brings about a surprisingly rapid and comprehensive healing which could not be achieved with the monotherapy (antimkycotic agent only).
  The success of the treatment was the clearer the more pronounced the initial findings had been.
  The invention claimed is:
  1. A method of treating a *Candida* mycosis further defined as vulvovaginal candidiasis and/or oropharyngeal candidiasis (oral thrush) comprising:
    obtaining a combination drug comprising an antimycotic agent and an epithelial cell or endothelial cell adhesion inhibitor, wherein the epithelial cell or endothelial cell adhesion inhibitor is Ilaprost, Cicaprost, Ticlopidine, or Clopidogrel; and
    topically treating mucosa of a subject having a *Candida* mycosis further defined as vulvovaginal candidiasis and/or oropharyngeal candidiasis with the combination drug, wherein the epithelial cell or endothelial cell adhesion inhibitor is applied to the mucosa in an amount that is between $1/5$ to $1/100$ of the epithelial cell or endothelial cell adhesion inhibitor's maximum daily systemic dose.
  2. The method of claim 1, wherein the *Candida* mycosis is vulvovaginal candidiasis.
  3. The method of claim 1, wherein the *Candida* mycosis is oropharyngeal candidiasis.
  4. The method of claim 1, wherein the antimycotic agent is an azole or conazole, a squalene epoxidase inhibitor, or a polyene antimycotic agent.
  5. The method of claim 4, wherein the antimycotic agent is Clotrimazole, Bifonazole, Miconazole, Econazole, Isokonazole, Itraconazole, Fenticonazole, Tioconazole, Serticonazole, Omoconazole, Oxiconazole, Fluconazole, Naftifin, Terbinafin Nystatin, Amphotericin B, Capsofungin, Natamycin, Ciclopirox, Butenafine, or Flucytosin.
  6. The method of claim 1, wherein the combination drug is further defined as an ointment, cream, lotion, gel, tincture, solution, vaginal suppository, vaginal, buccal or sublingual tablet, syrup, suspension, powder, spray, or aerosol.
  7. The method of claim 1, wherein the combination drug is comprised on an inert carrier.
  8. The method of claim 7, wherein the inert carrier is a vaginal ring, diaphragm, or tampon.

\* \* \* \* \*

UNITED STATES PATENT AND TRADEMARK OFFICE
CERTIFICATE OF CORRECTION

PATENT NO. : 8,552,042 B2  
APPLICATION NO. : 12/300578  
DATED : October 8, 2013  
INVENTOR(S) : Christian Noe et al.

Page 1 of 1

It is certified that error appears in the above-identified patent and that said Letters Patent is hereby corrected as shown below:

Title Page:

Item (73) Assignees, line 2
Change "Noe-Letschig," to -- Noe-Letschnig, --

Signed and Sealed this
Twenty-fourth Day of December, 2013

Margaret A. Focarino
*Commissioner for Patents of the United States Patent and Trademark Office*